United States Patent
Chen et al.

(10) Patent No.: US 10,053,696 B2
(45) Date of Patent: Aug. 21, 2018

(54) MIRNA-489 IN TREATMENT OF BREAST CANCER

(71) Applicant: University of South Carolina, Columbia, SC (US)

(72) Inventors: Hexin Chen, Columbia, SC (US); Yogin C. Patel, West Columbia, SC (US); Nirav R. Shah, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 15/411,314

(22) Filed: Jan. 20, 2017

(65) Prior Publication Data
US 2017/0211074 A1    Jul. 27, 2017

Related U.S. Application Data

(60) Provisional application No. 62/281,338, filed on Jan. 21, 2016.

(51) Int. Cl.
*C07H 21/02* (2006.01)
*C12N 15/113* (2010.01)
*A61K 31/713* (2006.01)
*A61K 45/06* (2006.01)
*C12Q 1/6886* (2018.01)

(52) U.S. Cl.
CPC ........ *C12N 15/1138* (2013.01); *A61K 31/713* (2013.01); *A61K 45/06* (2013.01); *C12Q 1/6886* (2013.01); *C12N 2310/141* (2013.01); *C12Q 2600/158* (2013.01); *C12Q 2600/178* (2013.01)

(58) Field of Classification Search
CPC .......................... C12N 2310/11; C12N 15/113
See application file for complete search history.

(56) References Cited

U.S. PATENT DOCUMENTS

| | | | | |
|---|---|---|---|---|
| 2011/0263675 A1* | 10/2011 | Federov | ................ | C12N 15/111 514/44 A |
| 2015/0216892 A1* | 8/2015 | Thibonnier | .......... | A61K 31/713 424/489 |
| 2015/0306077 A1* | 10/2015 | Ozpolat | ................ | C07D 209/14 514/300 |

FOREIGN PATENT DOCUMENTS

WO    WO 2009/044899 A1 *    9/2009    ........... C12N 15/113

OTHER PUBLICATIONS

Miller et al., The Journal of Biological Chemistry, vol. 283, No. 44, pp. 29897-29903, 2008.*
Gutierrez et al. (J. Clin. Oncol, 23, 2469-2476).*
Adachi R, Horiuchi S, Sakurazawa Y, Hasegawa T, Sato K and Sakamaki T. "ErbB2 down-regulates microRNA-205 in breast cancer." Biochemical and biophysical research communications. 2011; 411(4):804-808.
Arias-Romero Le, Saha S, Villamar-Cruz O, Yip SC, Ethier SP, Zbang ZY and Chernoff J. "Activation of Src by protein tyrosine phosphatase 1B Is required for EMB2 transformation of human breast epithelial cells." Cancer Res. 2009; 69(11):4582-4588.
Bailey ST, Westerling T and Brown M. "Loss of estrogen-regulated microRNA expression increases HER2 signaling and is prognostic of poor outcome in luminal breast cancer." Cancer Res. 2015; 75(2):436-445.
Bracken CP, Gregory PA, Kolesnikoff N, Bert AG, Wang J, Shannon MF and Goodall GJ. "A double-negative feedback loop between ZEB1-SIP1 and the microRNA-200 family regulates epithelial-mesenchymal transition" Cancer Res. 2008; 68(19):7846-7854.
Bunda S, Burrell K, Heir P, Zeng L, Alamsahebpour A, Kano Y, Raught B, Zhang ZY, Zadeh G and Ohh M. "Inhibition of SHP2-mediated dephosphorylation of Ras suppresses oncogenesis," Nature communications. 2015; 6:8859.
Chan G, Kalaitzidis D and Neel BG. "The tyrosine phosphatase Shp2 (PTPN11) in cancer." Cancer metastasis reviews. 2008; 27(2):179-192.
Chen H, Chung S and Sukumar S "HOXA5-induced apoptosis in breast cancer cells s mediated by caspases 2 and 8." Mol Cell Biol. 2004; 24(2):924-935.
Chen H, Lee JS, Liang X, Zhang H, Zhu T, Zhang 7, Taylor ME, Zahnow C, Feigenbaum L, Rein A and Sukumar S. "Hoxb7 inhibits transgenic HER-2/neu-induced mouse mammary tumor onset but promotes progression and lung metastasis." Cancer Res. 2008; 68(10):3637-3644.
Cheung TH, Quad NL, Charville GW, Liu L. Park L, Edalati A, Yoo B, Hoang P and Rando TA. "Maintenance of muscle stem-cell quiescence by microRNA-489." Nature. 2012; 482(7386):524-528.
Cittelly DM, Das PM, Salvo VA, Fonseca JP, Burow ME and Jones FE. "Oncogenic HER2{Delta}16 suppresses miR-15a/16 and deregulates BCL-2 to promote endocrine resistance of breast tumors." Carcinogenesis. 2010; 31(12)2049-2057.
Corsini LR, Bronte G, Tenasi M, Amodeo V, Fanale D, Fiorentino E, Cicero G, Bazan V and Russo A. "The role of microRNAs in cancer: diagnostic and prognostic biomarkers and targets of therapies." Expert opinion on therapeutic targets. 2012; 16 Suppl 2:S103-109.
De Rinaldis E, Gazinska P, Mera A, Modrusan Z, Fedorowicz GM, Burford B, Gillett C, Marra P, Grigoriadis A, Dornan D, Holmberg L, Pinder S and Tutt A. "Integrated genomic analysis of triple-negative breast cancers reveals novel microRNAs associated with clinical and molecular phenotypes and sheds light on the pathways they control. BMC genomics." 2013; 14:643.
Dvinge H, Git A, Graf S, Salmon-Divon M, Curtis C, Sottoriva A, Zhao Y, Hirst M, Armisen J, Miska EA, Chin SF, Provenzano E, Turashvili C. Green A, Ellis I, Aparicio S, et al. "The shaping and functional consequences of the microRNA landscape in breast cancer." Nature. 2013; 497(7449):378-382.

(Continued)

*Primary Examiner* — Amy H Bowman
(74) *Attorney, Agent, or Firm* — Dority & Manning, P.A.

(57) ABSTRACT

Breast cancer treatment methods and materials incorporating microRNA-489 are described. The methods and materials have been developed from identification of a double-negative feedback loop between miR-489 and the HER2-SHP2-MAPK signaling axis. The methods and materials may be particularly beneficial in treatment and diagnosis of HER2 positive breast cancers.

16 Claims, 8 Drawing Sheets

(56) References Cited

OTHER PUBLICATIONS

Fang X, Yoon J-G, Li L, Yu W, Shao J, Hua D, Zheng S, Hood L, Goodlett D, Foltz G and Lin B. "The SOX2 response program in glioblastoma multiforme: an integrated ChIP-seq, expression microarray, and microRNA analysis." BMC genomics. 2011; 12(1):11.

Feliciano A, Castellvi J, Artero-Castro A, Leal JA, Romagosa C, Hernandez-Losa J, Peg V, Fabra A, Vidal F, Kondoh H, Ramon YCS and Lleonad ME. "miR-125b Acts as a Tumor Suppressor in Breast Tumorigenesis via Its Novel Direct Targets ENPEP, CK2-alpha, CCNJ, and MEGF9." PLoS One. 2013; 8(10):e76247.

Ferrer-Soler L, Vazquez-Martin A, Brunet J, Menendez JA, De Llorens R and Colomer R. "An update of the mechanisms of resistance to EGER-tyrosine kinase inhibitors in breast cancer: Gefitinib (Iressa)-induced changes in the expression and nucleo-cytoplasmic trafficking of HER-ligands" (Review). Int 5 Mol Med. 2007; 20(1):3-10.

Filardo EJ, Quinn JA, Bland KI and A. Raymond Frackelton J. "Estrogen-Induced Activation of Erk-1 and Erk-2 Requires the G Protein-Coupled Receptor Homolog, GPR30, and Occurs via Trans-Activation of the Epidermal Growth Factor Receptor through Release of HB-EGF." Molecular Endocrinology. 2000; 14(10):1649-1660.

Finlay-Schultz J, Cittelly DM, Hendricks P, Patel P, Kabos P, Jacobsen BM, Richer JK and Sartorius CA. "Progesterone down regulation of miR-141 contributes to expansion of stem-like breast cancer cells through maintenance of progesterone receptor and Stat5a." Oncogene. 2014; 0.

Gajria D and Chandarlapaty S. "HER2-amplified breast cancer: mechanisms of trastuzumab resistance and novel targeted therapies." Expert review of anticancer therapy. 2011; 11(2):263-275.

Heiser LM, Sadanandam A, Kuo WL, Benz Sc, Goldstein TC, Ng S, Gibb WJ, Wang NJ, Ziyad S, Tong F, Bayani N, Hu Z, Billig Ji, Dueregger A, Lewis S, Jakkula L, et al. "Subtype and pathway specific responses to anticancer compounds in breast cancer." Proceedings of the National Academy of Sciences of the United States of America 2012; 109(8):2724-2729.

Higgins, Michaela J., and José Baselga. "Targeted therapies for breast cancer." The Journal of clinical investigation 121.10 (2011): 3797-3803.

Hu Yu, Zhu Q and Tang L. "MiR-99a antitumor activity in human breast cancer cells through targeting of mTOR expression." PLoS One. 2014; 9(3):e92099.

Ichikawa T, Sato F, Terasawa K, Tsuchiya S, Toi M, Tsujimoto G and Shimizu K "Trastuzumab produces therapeutic actions by upregulating miR-26a and miR-30b in breast cancer cells." PLoS One. 2012; 7(2):e31422.

Indira Chandran V, Eppenloerger-Castori S, Venkatesh T, Vine Kl and Ranson M. "HER2 and uPAR cooperativity contribute to metastatic phenotype of HER2-positive breast cancer." Oncoscience. 2015;2(3):207-224.

Iorio MV, Casalini P, Piovan C, Di Leva G, Merlo A, Triulzi T, Menard S, Croce CM and Tagliabue E. "microRNA-205 regulates HER3 in human breast cancer." Cancer Res. 2009; 69(6):2195-2200.

Jiang L, He D, Yang D, Chen Z, Pan Q, Mao A, Cai Y, Li X, Xing H, Shi M, Chen Y, Bruce IC, Wang T, Jin L, Qi X, Hua D. et al. "MiR-489 regulates chemoresistance in breast cancer via epithelial mesenchymal transition pathway." FEBS letters. 2014; 588(11):2009-2015.

Johnston RJ, Chang S, Etchberger JF, Ortiz CO and Hobert O. "MicroRNAs acting in a double-negative feedback loop to control a neuronal cell fate decision." Proceedings of the National Academy of Sciences of the United States of America. 2005; 102(35):12449-12454.

Kikkawa N, Hanazawa T, Fujimura L, Nohata N, Suzuki H, Chazono H, Sakurai D, Horiguchi S, Okamoto Y and Seki N. "miR-489 is a tumour-suppressive miRNA target PTPN11 in hypopharyngeal squamous cell carcinoma (HSCC)." British journal of cancer. 2010; 103(6):877-884.

Le MT, Hamar P, Guo C, Basar E, Perdigao-Henriques R, Balaj L and Lieberman J. "miR-200-containing extracellular vesicles promote breast cancer cell metastasis." J Clin Invest 2014; 124(12):5109-5128.

Lee JA, Lee HY, Lee ES, Kim I and Bas JW. "Prognostic Implications of MicroRNA-21 Overexpression in Invasive Ductal Carcinomas of the Breast," Journal of breast cancer. 2011; 14(4):269-275.

Lee Y, Ahn C, Han J, Choi H, Kim J, Yim J, Lee J, Provost P, Radmark O, Kim S and Kim VN. "The nuclear RNase III Drosha initiates microRNA processing." Nature. 2003; 425(6956):415-419.

Leivonen SK, Sahlberg KK, Makela R, Due EU, Kallioniemi O, Borresen-Dale AL and Perala M. "High-throughput screens identify microRNAs essential for HER2 positive breast cancer cell growth." Molecular oncology. 2014; 8(1):93-104.

Li SD and Huang L. "Targeted delivery of antisense oligodeoxynucleotide and small interference RNA into lung cancer cells." Molecular pharmaceutics. 2006; 3(5):579-588.

Li SD, Chono S and Huang L. "Efficient gene silencing in metastatic tumor by siRNA formulated in surface-modified nanoparticles." Journal of controlled release : official journal of the Controlled Release Society. 2008; 126(1):77-84.

Liu S, Jin K, Hui Y, Fu J, Jie C, Feng S, Reisman D, Wang Q, Fan D, Sukumar S and Chen H. "HOXB7 promotes malignant progression by activating the TGFbeta signaling pathway." Cancer Res. 2015; 75(4):709-719.

Lowery AJ, Miller N, Devaney A, McNeill RE, Davoren PA, Lemetre C, Benes V, Schmidt S, Blake J, Ball G and Kerin MJ. "MicroRNA signatures predict oestrogen receptor, progesterone receptor and HER2/neu recanor status in breast cancer." Breast Cancer Res. 2009; 11(3):R27.

Matozaki T, Murata Y, Saito Y, Okazawa H and Ohnishi H. Protein tyrosine phosphatase SHP-2: a proto-oncogene product that promotes Ras activation. Cancer science. 2009; 100(10):1786-1793.

Mattie MD, Benz CC, Bowers J, Sensinger K, Wong L, Scott GK, Fedele V, Ginzinger D, Getts R and Haqq C. "Optimized high-throughput microRNA expression profiling provides novel biomarker assessment of clinical prostate and breast cancer biopsies." Molecular cancer. 2006; 5:24.

Muller PC, Clarke J, Koru-Sengul T, Brinkman J and El-Ashry D. "A novel MAPK-microRNA signature is predictive of hormone-therapy resistance and poor outcome in ER-positive breast cancer." Clin Cancer Res. 2015; 21(2):373-385.

Mohi MG and Neel BG. "The role of Shp2 (PTPN11) in cancer." Current opinion in genetics & development. 2007; 17(1):23-30.

Mulrane L, Gallagher WM and O'Connor DP. "A novel mechanism of regulation of the anti-metastatic miR-31 by EMSY in breast cancer." Breast cancer research : BCR. 2014; 16(6):467.

Oh AS, Lorain LA, Holloway JN, Miller DL, Kern FG and El-Ashry D. "Hyperactivation of MAPK induces loss of ERalpha expression in breast cancer cells." Molecular endocrinology (Baltimore, Md. 2001; 15(8):1344-1359.

Pinatel EM, Orso F, Penna E, Cimino D, Elia AR, Circosta P, Dentelli P, Brizzi MF, Proven P and Taverna D. "miR-223 is a coordinator of breast cancer progression as revealed by bioinformatics predictions." PLoS One. 2014; 9(1):e84859.

Pogribny IP, Filkoaski JN, Tryndyak VP, Golubov A, Shpyleva SI and Kovalchuk O. "Alterations of microRNAs and their targets are associated with acquired resistance of MCF-7 breast cancer cells to cisplatin." International journal of cancer Journal international du cancer. 2010; 127(8):1785-1794.

Qian B, Katsaros D, Lu L, Pred M, Durando A, Arisio R, Mu L and Yu H. "High miR-21 expression in breast cancer associated with poor disease-five survival in early stage disease and high TGF-β1." Breast cancer research and treatment. 2009; 117(1):131-140.

Santen RJ, Fan P, Zhang Z, Bao Y. Song RX and Yue W. "Estrogen signals via an extra-nuclear pathway involving waiving IGF-1R and EGFR in tamoxifen-sensitive and -resistant breast cancer cells." Steroids. 2008.

Shah, Nirav R., and Hexin Chen. "MicroRNAs in pathogenesis of breast cancer: Implications in diagnosis and treatment" World J Clin Oncol 5.2 (2014): 48-60.

(56) References Cited

OTHER PUBLICATIONS

Talotta F, Cimmino A, Matarazzo MR, Casalino L, De Vita G, D'Esposito M, Di Lauro R and Verde P. "An autoregulatory loop mediated by miR-21 and PDCD4 controls the AP-1 activity in RAS transformation." Oncogene. 2009; 28(1):73-84.

Wang Emily, Shizhen, and Ren-Jong Lin. "MicroRNA and HER2-overexpressing cancer." Microrna 2.2 (2013): 137-147.

Wee EJ, Peters K, Nair SS, Hulf T, Stein S, Wagner S, Bailey P, Lee SY, Qu WJ, Brewster B, French JD, Dobrovic A, Francis GD, Clark SJ and Brown MA "Mapping the regulatory sequences controlling 93 breast cancer-associated miRNA genes leads to the identification of two functional promoters of the Hsa-mir-200b cluster, methylation of which is associated with metastasis or hormone receptor status in advanced breast cancer," Oncogene, 2012; 31(38):4182-4195.

Wu H, Xiao Z, Zhang H, Wang K, Liu W and Hao Q. "MiR-489 modulates cisplatin resistance in human ovarian cancer cells by targeting Akt3." Anticancer Drugs. 2014; 25(7):799-809.

Yang X, Lin X, Zhong X, Kaur S, Li N, Liang S, Lassus H, Wang L, Katsaros D, Montone K, Zhao X, Zhang Y, Butzow R, Coukos G and Zhang L. "Double-negative feedback loop between reprogramming factor LIN28 and microRNA let-7 regulates aldehyde dehydrogenase 1-positive cancer stem cells." Cancer Res, 2010; 70(22):9463-9472.

Zhang SQ, Tsiaras WG, Araki T, Wen G, Minichiello L, Klein R and Neel BG. "Receptor-specific regulation of phosphatidylinositol 3'-kinase activation by the protein tyrosine phosphatase Shp2." Mol Cell Biol. 2002; 22(12):4062-4072.

Zhou J, Tian Y, Li J, Lu B, Sun M, Zou Y, Kong R, Luo Y, Shi Y, Wang K and Ji G. "miR-206 is down-regulated in breast cancer and inhibits cell proliferation through the up-regulation of cyclinD2." Biochem Bk2phLs Res Commun. 2013; 433(2):207-212.

Zhu X and Verma S. "Targeted therapy in her2-positive metastatic breast cancer: a review of the literature." Current oncology. 2015; 22(Suppl 1):S19-28.

* cited by examiner

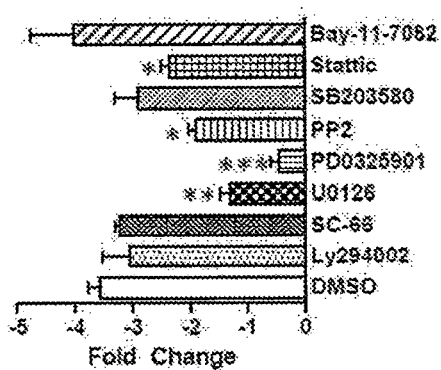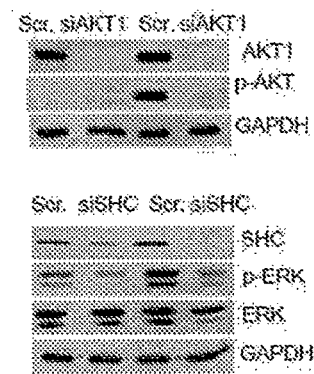
FIG. 7  FIG. 8
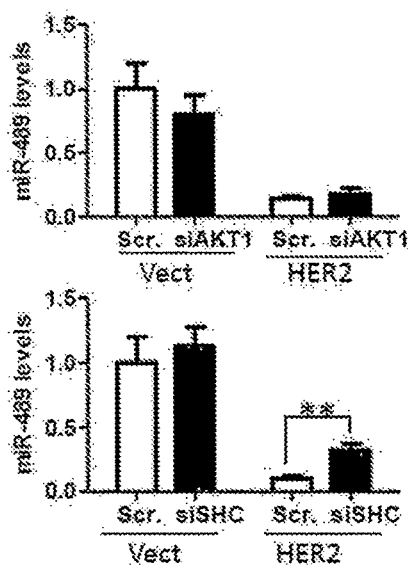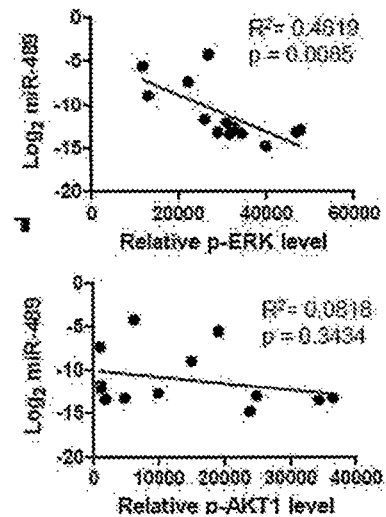
FIG. 9  FIG. 10

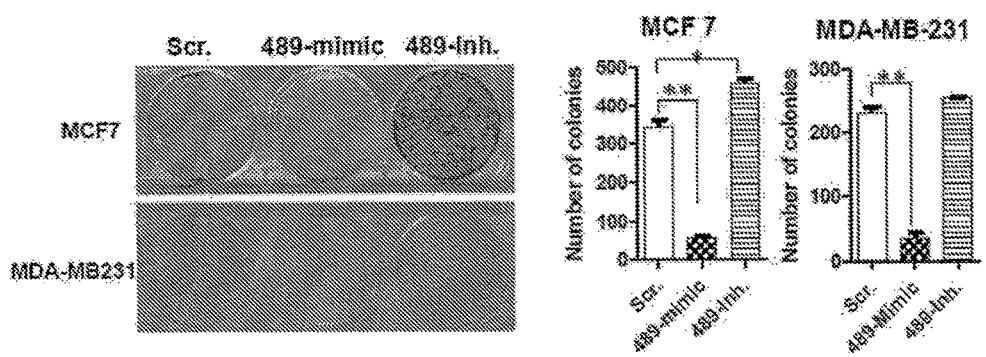
FIG. 13
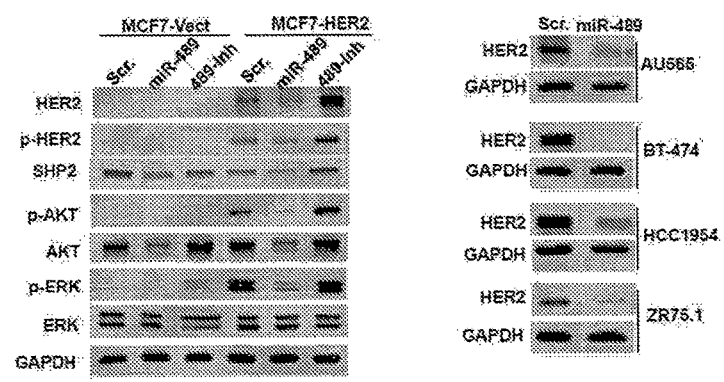 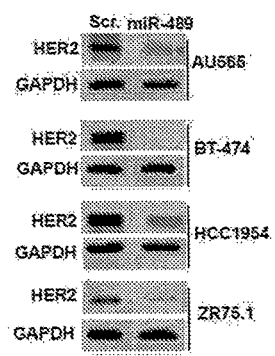
FIG. 14     FIG. 15

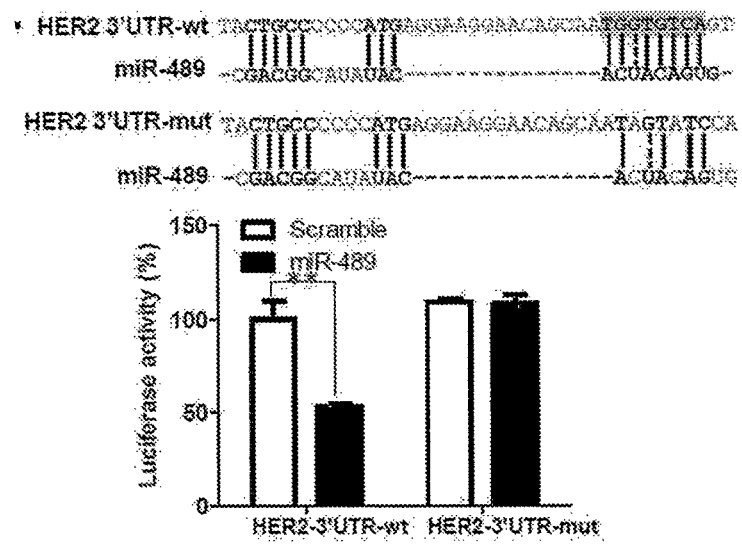
FIG. 16
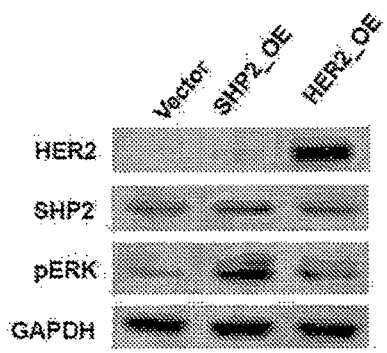 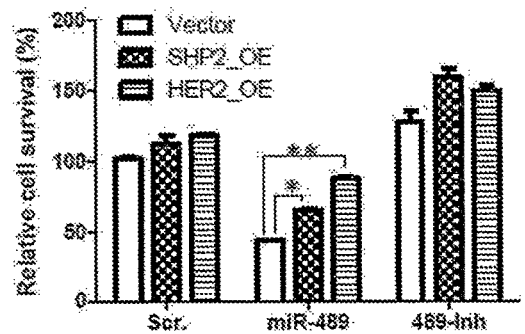
FIG. 17　　　　FIG. 18

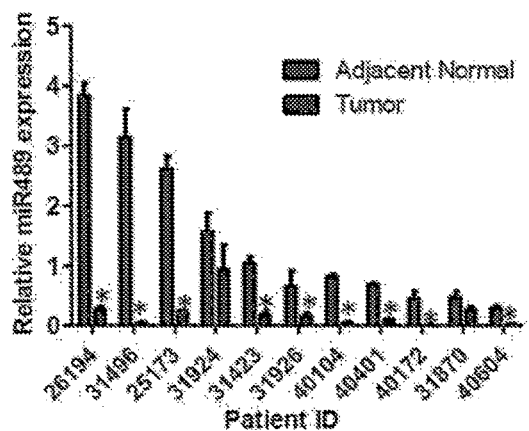
FIG. 22
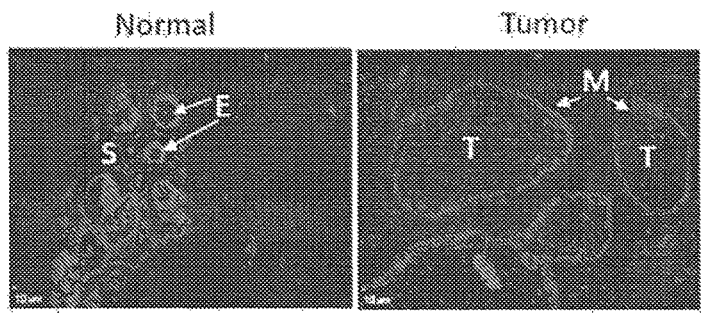
FIG. 23
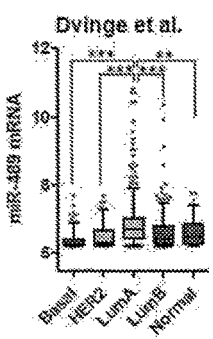 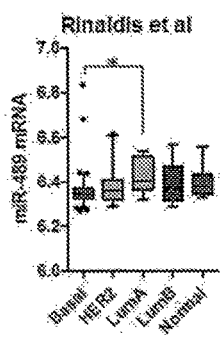 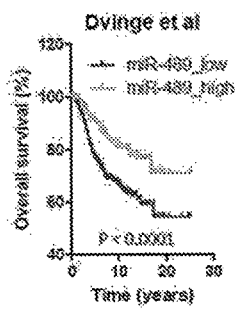 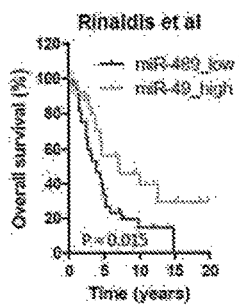
FIG. 24  FIG. 25

SEQUENCE LISTING

```
<160> NUMBER OF SEQ ID NOS: 5

<210> SEQ ID NO 1
<211> LENGTH: 84
<212> TYPE: DNA
<213> ORGANISM: Homo sapiens

<400> SEQUENCE: 1
gtggcagctt ggtggtcgta tgtgtgacgc catttacttg aacctttagg agtgacatca      60
catatacggc agctaaactg ctac                                             84

<210> SEQ ID NO 2
<211> LENGTH: 84
<212> TYPE: RNA
<213> ORGANISM: Homo sapiens

<400> SEQUENCE: 2
guggcagcuu gguggucgua ugugugacgc cauuuacuug aaccuuuagg agugacauca      60
cauauacggc agcuaaacug cuac                                             84

<210> SEQ ID NO 3
<211> LENGTH: 39
<212> TYPE: DNA
<213> ORGANISM: Homo sapiens

<400> SEQUENCE: 3
tactgccccc catgaggaag gaacagcaat ggtgtcagt                             39

<210> SEQ ID NO 4
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
cgacggcaua uacacuacag ug                                               22

<210> SEQ ID NO 5
<211> LENGTH: 38
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 5
tactgccccc catgaggaag gaacagcaat agtatcca                              38
```

MIRNA-489 IN TREATMENT OF BREAST CANCER

CROSS REFERENCE TO RELATED APPLICATION

This application claims filing benefit of U.S. Provisional Patent Application Ser. No. 62/281,338 having a filing date of Jan. 21, 2016, which is incorporated herein by reference.

GOVERNMENT SUPPORT CLAUSE

This invention was made with government support under grant no. 5R01CA178386-03 awarded by the National Institutes of Health. The government has certain rights in the invention.

BACKGROUND

Breast cancer is a heterogeneous disease with several subtypes identified by unique molecular signatures. Nearly, 30% of total breast cancer patients overexpress human epidermal growth factor receptor 2 (ErbB2 or HER2). HER2 is a receptor tyrosine kinase and is associated with poor prognosis and outcome. It is well documented that overexpression of HER2 promotes aggressive tumor phenotype, increases metastasis and decreases overall survival of patients.

Trastuzumab, a monoclonal antibody to HER2, accrues significant clinical benefit in the metastatic and adjuvant settings. However, some patients suffer disease recurrence despite adjuvant trastuzumab therapy, and many patients with metastatic disease do not respond to therapy or develop refractory disease within 1 year of treatment.

Dysregulation of several microRNAs (miRNAs) is also known to play a role in breast cancer progression and metastasis. MicroRNAs are small (18-25 nucleotide) long non-coding, single stranded RNAs that regulate the expression of various genes at post-transcriptional level mostly by binding to a partially complementary site on the 3'UTR region of target mRNA. It has been suggested that HER2 regulates the expression of certain miRNAs to promote cell proliferation and tumorigenesis. For instance, down-regulation of miR-205 by HER2 has been shown to enhance tumorigenesis in breast cancer. It has also been found that hyper-methylation of miR-200b promoter is associated with higher HER2 expression, and aberrant expression of some miRNAs by HER2 has been shown to enhance resistance to chemotherapeutic drugs. However, it still remains largely unknown how HER2 promotes tumor progression via regulation of specific microRNAs as well as other miRNAs that may be involved in the process.

What are needed in the art are methods and materials for use in diagnosis and treatment of breast cancer. For instance, identification of specific molecular factors that can regulate HER2 signaling would be of great benefit for more targeted and efficient therapy against many breast cancers including HER2 positive breast cancer.

SUMMARY

Aspects and advantages of the invention will be set forth in part in the following description, or may be obvious from the description, or may be learned through practice of the invention.

In one embodiment, disclosed is a method for decreasing cancer cell proliferation, e.g., in treatment of a breast cancer. For example, a method can decrease cell proliferation of breast cancer cells exhibiting hyperactivation of the ERK½ MAPK signature such as are present in HER2 positive and basal-like breast cancers.

A treatment method can include delivery of a polynucleotide comprising a microRNA-489 nucleic acid sequence (also referred to herein as miR-489 and miRNA-489) to a population of breast cancer cells. For example, a DNA-based construct that encodes an miR-489 can be delivered to a cell for transcription within the cell. In one embodiment an RNA construct can be delivered to a cell, e.g., a primary miRNA construct (pri-miRNA) or a precursor stem-loop RNA construct (pre-miRNA) that includes an miRNA-489 in the construct. In one embodiment a mature single strand miR-489 can be delivered to a cell.

In one embodiment, a method can include diagnosing breast cancer. For instance, a method can include determining the ratio of miR-489 to HER2 in a sample to diagnose cancer in a subject from which the sample is obtained or derived. The method can also include treating the cancer through delivery of a polynucleotide comprising a microRNA-489 nucleic acid sequence to the cancer cells.

These and other features, aspects and advantages of the present disclosure will become better understood with reference to the following description and appended claims.

BRIEF DESCRIPTION OF THE FIGURES

A full and enabling disclosure of the present invention, including the best mode thereof, directed to one of ordinary skill in the art, is set forth in the specification, which makes reference to the appended figures. Unless otherwise noted, **, $p<0.01$; *, $p<0.05$; and ***, $p<0.001$.

FIG. 7 presents the effects of HER2- downstream signaling inhibitor treatments on the expression of miR-489 in MCF-7 HER2 cells. MCF-7 HER2 cells were treated with each of the following inhibitors Bay-11 7082 (2 µM), Stattic (2 µM), SB-203580 (10 µM), PP2 (10 µM), PD0325901 (10 µM), U0126 (10 µM), SC-66 (2 µM), LY294002 (10 µM) for 24 h.

FIG. 8 is a Western blot showing the effect of siAKT on the expression of AKT, pAKT and effect of siSHC on SHO, p-ERK and ERK expression.

FIG. 9 presents the effects of siRNA-mediated blockage of AKT (top) and MAPK (bottom) signaling on the expression of miR-489.

FIG. 10 presents the Pearson analysis of the Correlation between p-AKT (bottom) or p-ERK½ (top) and mature miR-489 in breast cancer lines.

FIG. 13 presents colony formation assay on MCF7 (top image and left graph) and MDA-MB231 cells (bottom image and right graph) transfected with scramble miR489, mimic miR-489 or inhibitor mir-489.

FIG. 14 presents effects of miR-489 and inhibitor treatment on HER2-downstream signaling. Western blot analysis was performed after MCF-7 vector/HER2 cells were transfected for 72 hrs.

FIG. 15 presents Western blot analysis of other breast cancer cell lines treated with miR-489 mimic—these cell lines also showed reduction in HER2 expression.

FIG. 16 presents a schematic representation of the HER2 mRNA (wild type (wt) and mutant (mut)) with putative miR-489 binding site in the 3' UTR, where the seed region is highlighted. MCF7 HER2 cells were co-transfected with either of miR-489 expressing vector or empty vector and renilla expressing vector for 48 h. Firefly luciferase was measured for each condition and normalized with renilla luciferase. Normalized luciferase activity was compared with WT-3'UTR and Mutant 3' UTR of HER2 (graph).

FIG. 17 presents a Western blot showing expression of SHP2 and HER2 in SHP2_OE and HER2_OE MDA-MB231 cells.

FIG. 18 presents results of an MTT assay showing relative cell survival of vector control, SHP2_OE or HER2_OE cells transfected with scramble, mimic miR-489 or inhibitor miR-489.

FIG. 22 presents the real-time RT- PCR analysis of miR-489 in breast cancer tumor tissues and their adjacent normal tissues from 11 breast cancer patients.

FIG. 23 presents FISH analysis of miR-489 expression in normal breast tissue and adjacent tumor tissues. E, normal epithelial cells; S, stromal cells; M, myoepithelial cells; T, tumor cells.

FIG. 24 presents a comparison of relative expression levels of miR-489 in breast cancer subtypes using the one-way ANOVA analysis. The microarray data was extracted from previous publication as noted.

FIG. 25 presents a comparison showing that the expression status of miR-489 predicts clinical outcome. Patient survival was estimated using the Kaplan-Meier method and compared with log-rank tests. The Y axis represents the probability of overall survival.

DETAILED DESCRIPTION

It is to be understood by one of ordinary skill in the art that the present discussion is a description of exemplary embodiments only, and is not intended as limiting the broader aspects of the present disclosure. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Figure 1:
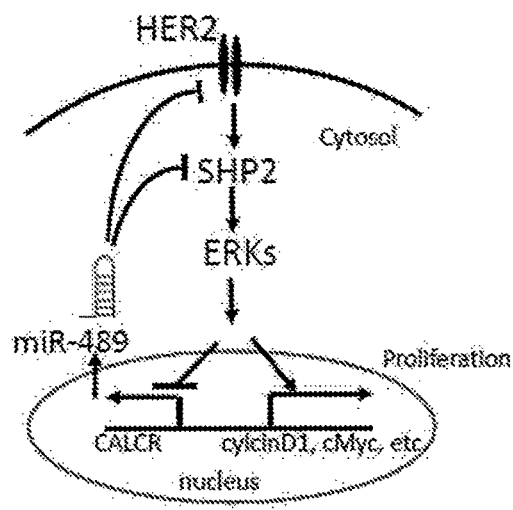
FIG. 1 presents a general feedback loop in which HER2 signaling through SHP2 and ERK promotes cell proliferation and inhibits miR-489 expression, and in which miR-489 down-regulates both HER2 and SHP2 directly to inhibit cell proliferation.

The present disclosure is generally directed to methods and materials for use in breast cancer treatment and diagnosis. The methods and materials have been developed from identification of a double-negative feedback loop between miR-489 and the HER2-SHP2-MAPK signaling axis as illustrated in FIG. 1 and are generally directed to determining and/or increasing the level of miRNA-489 in breast cancer cells.

As utilized herein, the term miRNA-489 is intended to refer to natural miR-489 as well as mimics of endogenous miR-489. As used herein, the term "microRNA mimic" refers to synthetic non-coding RNAs that are capable of entering the RNAi pathway and regulating gene expression. As used herein, "synthetic microRNA" refers to any type of RNA sequence other than endogenous microRNA. microRNA mimics imitate the function of endogenous microRNAs and can be designed as mature molecules, double-stranded molecules, or miRNA precursors (e.g., pri- or pre-microRNAs). MicroRNA mimics can be include synthetic and/or natural, modified and/or unmodified RNA, DNA, RNA-DNA hybrids or alternative nucleic acid chemistries as are generally known in the art.

The methods can beneficially be utilized in one embodiment to regulate cancer cell proliferation and tumor growth in breast cancer. As a general model, the double-negative feedback loop is advantageous in allowing a system to remain reversible. In the present case, it is believed that the HER2-SHP2-MAPK/miR-489 feedback loop is involved in regulation of quiescence/proliferation phonotypical transition in cancer cells. Specifically, HER2 expression is understood to be associated with higher cell proliferation, whereas miR-489 expression is understood to be associated with slow proliferation or quiescent status. Given that a double-negative feedback loop generally allows the maintenance of bi-stable states, it is believed that the ratio of HER2/miR-489 is important for generation of tumor heterogeneity and determination of tumor behaviors.

Although the data and the majority of the discussion herein are directed to control of miR-489 expression in HER2-positive tumors, the present disclosure is not intended to be limited to HER2-positive cancers. miR-489 concentration can be advantageously increased according to disclosed methods in many different breast cancers independent of their HER2 expression status.

miR-489 is mainly regulated via the MEK-ERK pathway, which can be activated by many overexpressing oncogenes, receptors, or cytokines. For example, expression of multiple members of the epidermal growth factor receptor family (HER1, HER2, HER3) and estrogen receptor (ER) is present in most breast cancer cells, and these receptors have all been shown to activate the MEK-ERK pathway. This may explain why miR-489 is broadly down-regulated in breast cancer cells compared to their adjacent normal tissues (as described further in the example section herein), especially in HER2-positive and basal subtypes of breast cancers. Hyperactivation of ERK½ MAPK signaling occurring downstream of EGFR or HER2 in breast cancer can induce loss of ER expression leading to establishment of ER-negative phenotype. Cancers with hyperactivation of ERK½ MAPK signature are associated with adverse clinical features and especially enriched for basal-like and HER2-positive subtypes. Significantly, the expression levels of miR-489 are lower in basal-like and HER2-positive subtypes compared to luminal subtypes of breast cancers. Given that the expression levels of miR-489 can be strongly correlated with tumor aggressive phenotypes, utilization of miR-489 as a therapy as disclosed herein can be of benefit not just in HER2/neu-overexpressing tumors, but also in broader subsets of patients.

As described in further detail below, miR-489 is specifically downregulated by HER2-downstream signaling, especially through the MAPK pathway. Methods as disclosed herein that can be utilized to restore concentration of or induce overexpression of miR-489 in breast cancer cells can inhibit cell growth in vitro and can decrease tumorigenecity and tumor growth rate.

Mechanistically, increased presence of miR-489 can lead to decreased levels of HER2 as well as SHP2 and thus can attenuate HER2-downstream signaling. Furthermore, HER2 can be a direct target of miR-489 and therefore HER2-SHP2-MAPK and miR-489 signaling pathways can form a mutual regulatory loop. Overall, miR-489 can act as a tumor suppressor microRNA by simultaneously targeting HER2 and its downstream gene Shp2. Loss of miR-489 expression as is found in HER2 positive as well as other breast cancers results in both HER2 overexpression and enhanced downstream signaling, which may account for resistance or diminished response to HER2-targeted therapy in breast cancer patients.

Through increase of the concentration of miRNA-489, a variety of aspects of the disease state can be ameliorated including uncontrolled cell proliferation, invasion and metastasis. Beneficially, increased levels of miRNA-489 can inhibit cell growth in all cell lines examined and is understood to have broad application to HER2 positive as well as other breast cancers. For instance, and as described further herein, restoration of miR-489 expression in HER2- overexpressing breast cancer cells can strongly inhibit cell proliferation both in vitro and in vivo. In addition, and different from many tumor suppressors that normally induce cell cycle arrest and apoptosis, increase of miR-489 can dramatically reduce ki-67 positive population, but is understood to not induce apoptosis. Moreover, and without wishing to be bound to any particular theory, it is believed that miR-489 can modulate HER2 signaling networks via simultaneously targeting multiple downstream genes during breast carcinogenesis.

miR-489 concentration in a cancer cell can be increased through delivery of miR-489 as an RNA precursor for processing within the cell, in a mature form of the microRNA or as a component of an expression vector from which pri-miR-489, pre-miR-489, or miR-489 can be expressed. Nucleic adds comprising the mature or precursor forms of miRNA-489 together with additional flanking nucleotides 5' or 3' to the miRNA-489 sequence may be used.

Sequences for miR-489 are available from known databases such as, for example, from the database maintained by the National Center for Biotechnology Information (NCBI) data at ncbi.nlm.nih.gov. For example, miR-489 nucleic acids can include the human DNA sequence as follows (NCBI accession number NR 030164.1):

```
                                          (SEQ ID NO: 1)
     gtggcagctt ggtggtcgta tgtgtgacgc catttacttg aacctttagg agtgacatca catatacggc agctaaactg ctac
```

In one embodiment, the miR-489 sequence can be the mature RNA sequence as follows (miRBase accession number M10003124):

```
                                          (SEQ ID NO: 2)
     guggcagcuu gguggucgua ugugugacgc cauuuacuug aaccuuuacc agugacauca cauauacggc agcuaaacug cuac
```

Figure 2:
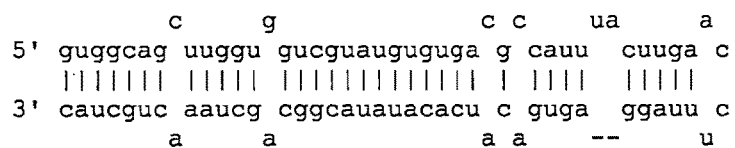
FIG. 2 presents a stem-loop structure of a mature miR-489 (SEQ ID NO: 2) as may be utilized in conjunction with disclosed methods.

FIG. 2 illustrates the stem-loop structure of a mature RNA of SEQ ID NO: 2).

Like most miRNAs, miR-489 is highly conserved between different species. Thus, while the miRNA for use in a protocol may be derived from the species of the subject to be treated (e.g., human), or constitute a sequence identical to miRNA from that species, this need not be the case in view of the high level of sequence conservation of miRNA sequences between species.

Mature miRNAs are generated in vivo from RNA transcripts (pri-miRNAs) that usually contain several hundred nucleotides transcribed from regions of non-coding DNA. Pri-miRNAs are processed in the nucleus by RNase III endonuclease to form stem-loop precursors (pre-miRNAs) of approximately 70 nucleotides. Pre-miRNAs are actively transported into the cytoplasm where they are further processed into short RNA duplexes, typically of 21-23 nucleotides, one of which represents the functional mature miRNA strand. The administration of pri-miRNA and/or pre-miRNA precursors is contemplated herein, wherein the pri-miRNA or pre-miRNA is cleaved and intracellularised to generate a functional miRNA.

In addition to a full-length miR-489 molecule, such as that shown in SEQ ID NO: 1 and SEQ ID NO:2, the term "miR-489" also includes fragments of an miR-489 molecule provided the fragments are functional fragments. The term "fragment" of an miRNA molecule means a portion of the full-length molecule. The size of the fragment is limited only in that it must be a functional fragment, that is, able to modulate components of ERK½ MAPK signaling pathways and have therapeutic utility against breast cancer cells as described herein.

Embodiments also contemplate the administration of miRNA mimics of miR-489. Mimics include nucleotide sequences that function in a fashion that is substantially similar to sequences of miRNA disclosed herein. In some embodiments, the mimic miRNA includes a sequence displaying at least 80% sequence identity to the sequence of human miR-489 (SEQ ID NO: 1 or SEQ ID NO: 2). In some embodiments, the miRNA includes a sequence displaying at least 90% sequence identity to SEQ ID NO: 1 or SEQ ID NO: 2. In some embodiments, the miRNA includes a sequence displaying at least 91%, 92%, 93%, 94%, 95%, 96%, 97%, 98% or 99% sequence identity to SEQ ID NO: 1 or SEQ ID NO: 2.

miRNA-489 mimics are available and known in the art, for instance from Dharmacon, a division of GE Healthcare. An miRNA-489 mimic can include modifications as compared to an endogenous miRNA, such as natural residues or non-natural residues substituted at one or more positions with respect to the endogenous miR-489 sequence. Examples of nucleotides that can be employed in miR-489 mimics can include, without limitation, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine.

miRNA-489 may be prepared using methods available in the art, for example, by expression from an expression vector encoding the sequence of the miR-489 nucleic acid or a complement thereof. Alternatively, it may be prepared by chemical synthesis using naturally-occurring nucleotides, modified nucleotides or any combinations thereof. In some embodiments, the miR-489 nucleic acids can include modified nucleotides or non-phosphodiester bonds, for example, that are designed to increase biological stability of the miR-489 nucleic acids. For example, the miR-489 nucleic acids can be peptide nucleic acids that have peptide bonds rather than phosphodiester bonds.

miRNA-489 nucleic acids may be made using any technique known to one of ordinary skill in the art such as, for example and without limitation, chemical synthesis, enzymatic production or biological production. Non-limiting methods for synthesizing nucleic acids include in vitro chemical synthesis using phosphotriester, phosphite, or phosphoramidite chemistry and solid phase techniques as are known in the art, or using deoxynucleoside H-phosphonate intermediates as described in U.S. Pat. No. 5,705,629, incorporated herein by reference. Various different mechanisms of oligonucleotide synthesis have been disclosed in for example, U.S. Pat. Nos. 4,659,774; 4,816,571; 5,141,813; 5,264,566; 4,959,463; 5,428,148; 5,554,744; 5,574,146; 5,602,244; each of which is incorporated herein by reference.

An miRNA-489 nucleotide for use as described herein can take the form of a nucleic acid that includes a sequence that is complementary to miRNA-489 mature and/or precursor sequences. This contemplates that miRNA-489 may be synthesized in vivo. One of ordinary skill is capable of designing such complementary sequences based on the knowledge of the miRNA-489 nucleotide sequence (mature and/or precursor) provided herein or otherwise known in the art. In those embodiments in which miRNA-489 is to be synthesized in vivo, a subject may be administered a nucleic acid comprising its complementary sequence, optionally operably linked to regulatory nucleic acid sequences such as promoters and enhancers. The nucleic acids may be provided in vectors such as but not limited to viral vectors (e.g., adenovirus vectors).

An miRNA-489 nucleic acid sequence can generally range in length from about 20 to about 100 nucleotides, or about 20 to about 50 nucleotides, or about 20 nucleotides to about 30 nucleotides. In some embodiments, a nucleic acid sequence may be more than 100 nucleotides, including for example if it is presented in a vector such as a virus or virus like construct for in vivo production. In some embodiments, the miRNA-489 nucleic acid sequence can be isolated. This means that the miRNA-489 is physically separated from its natural environment which may be genomic DNA, or a cell, or a cell lysate, or an in vitro chemical reaction mixture. In some embodiments, a population of isolated nucleic acids can be at least about 90% homogenous, and can be at least about 95, 96, 97, 98, 99, or 100% homogenous with respect to sequence. In some embodiments, a nucleic acid is isolated as it has been synthesized in vitro separate from other nucleic acids.

miRNA may be directly administered to a subject in need of treatment or the administration may be ex vivo administration to cells or tissue derived from a subject. For instance, a cancer cell can be directly contacted with the miR-489, i.e. the miR-489 can be applied directly to a cell, or alternatively the miR-489 may be combined with the cell indirectly, e.g. by locating the miR-489 in the bloodstream of a subject, which then can carry the miR-489 to the cell. In one embodiment, a sample may be removed from a subject and combined with an miRNA-489 ex viva prior to returning at least a portion of the sample back to the subject.

The miRNA-489 may be administered in conjunction with agents capable of stimulating or enhancing the expression or activity of the miRNA-489. Such agents may be proteinaceous, non-proteinaceous or nucleic acid-based and include, for example, molecules and compounds capable of binding to the regulatory sequences of miRNA genes to thereby induce or enhance the level of endogenous expression of the miRNA. Those skilled in the art will appreciate that the scope of the invention is not so limited and any agents capable of stimulating or enhancing miRNA expression or activity are contemplated and fall within the scope of the present disclosure.

The miRNA-489 may optionally be inked to an agent capable of delivering the miRNA to the desired site. In some embodiments the link between the miRNA and the additional agent can be a cleavable link The presence of a cleavable link allows for cleavage of the miRNA from the additional agent, for example after internalization into cancer cells.

In one embodiment, miR-489 may be utilized in conjunction with a suitable expression system, and a quantity of miR-489 nucleic acids can be generated from such expression systems. Recombinant expression is usefully accomplished using a vector, such as a plasmid. The vector can include a promoter operably linked to nucleic acid encoding a miR-489 nucleic acid. The vector can also include other elements required for transcription and translation. As used herein, vector refers to any carrier containing exogenous DNA. Thus, vectors are agents that transport the exogenous nucleic acid into a cell without degradation and include a promoter yielding expression of the nucleic acid in the cells into which it is delivered. Vectors include but are not limited to plasmids, viral nucleic acids, viruses, phage nucleic acids, phages, cosmids, and artificial chromosomes. A variety of prokaryotic and eukaryotic expression vectors suitable for carrying, encoding and/or expressing miR-489 nucleic acids are encompassed herein. Such expression vectors include, for example, pET, pET3d, pCR2.1, pBAD, pUC, and yeast vectors.

The expression cassette, expression vector, and sequences in the cassette or vector can be heterologous. As used herein, the term "heterologous" refers to a construct that has been manipulated in some way as compared to a naturally occurring expression system. For example, a heterologous promoter can be a promoter that is not naturally linked to a nucleic acid of interest, or that has been introduced into cells by cell transformation procedures. A heterologous nucleic acid or promoter can also encompass a nucleic acid or promoter that is native to an organism but that has been altered in some way (e.g., placed in a different chromosomal location, mutated, added in multiple copies, linked to a non-native promoter or enhancer sequence, etc.). Heterologous nucleic acids may comprise sequences that comprise cDNA forms; the cDNA sequences may be expressed in either a sense (to produce mRNA) or anti-sense orientation (to produce an anti-sense RNA transcript that is complementary to the mRNA transcript).

Viral vectors that can be employed include those relating to lentivirus, adenovirus, adeno-associated virus, herpes virus, vaccinia virus, polio virus, AIDS virus, neuronal trophic virus, Sindbis and other viruses. Also useful are any viral families which share the properties of these viruses which make them suitable for use as vectors.

A variety of regulatory elements can be included in an expression cassette and/or expression vector, including promoters, enhancers, translational initiation sequences, transcription termination sequences and other elements.

The expression of miR-489 from an expression cassette or expression vector can be controlled by any promoter capable of expression in prokaryotic cells or eukaryotic cells. Examples of prokaryotic promoters that can be used include, but are not limited to, SP6, T7, T5, tac, bla, trp, gal, lac, or maltose promoters. Examples of eukaryotic promoters that can be used include, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE. Vectors for bacterial expression include pGEX-5X-3, and for eukaryotic expression include pCIneo-CMV.

The expression cassette or vector can include a nucleic acid sequence encoding a marker product. This marker product can be used to determine if the gene has been delivered to the cell and once delivered is being expressed. Exemplary marker genes include the *E. coli* lacZ gene which encodes β-galactosidase and green fluorescent protein.

The miR-489 nucleic acid molecule, expression cassette and/or vector can be introduced to a cell by any method including, but not limited to, calcium-mediated transformation, electroporation, microinjection, lipofection, particle bombardment and the like. The miR-489 can generally be delivered in a physiological solution such as saline or buffered saline. The miR-489 can also be delivered in a vehicle such as a population of liposomes, exosomes or microvesicles.

In one embodiment, transgenic cells with a heterologous expression cassette or expression vector that expresses miR-489 can be administered to a subject and the exosomes produced by the transgenic cells can deliver miR-489 to tumor and cancer cells in the subject. Exosomes can be produced by many different types of cells including immune cells such as B lymphocytes, T lymphocytes, dendritic cells (DCs) and mast cells. Exosomes are also produced, for example, by glioma cells, platelets, reticulocytes, neurons, intestinal epithelial cells, tumor cells, HELA cells, human embryonic kidney cells (HEK cells), B2M17 cells, Bend3 cells, primary bone marrow-derived dendritic cells, BV-2 microglia cells and EURO2A cells. Any of these cells can be host cells or transgenic cells that express miR-489 (e.g., from a heterologous expression cassette or a heterologous expression vector).

In one embodiment, the microRNA can be formulated for delivery to cancer cells in conjunction with a delivery vehicle such as a liposome, microvesicle, exosome, or another micro- or nano-sized delivery vehicle capable of delivery of a payload to a cancer cell. For example, exosomes or microvesicles containing miR-489 can be isolated from a host or transgenic cell and the miR-489 loaded delivery vehicle can then be formulated into a suspension for administration to a subject such as a cancer patient. Such miR-489 loaded exosomes and/or microvesicles can be obtained from any suitable cell type as discussed above, or by isolation from physiological fluids, cell culture media, or tissue supernatants. Alternatively, a delivery vehicle, e.g., exosomes, microvesicles, or nanovesicles, can be loaded with exogenous miR-489, followed by formulation into a suspension for delivery to a subject.

In one embodiment, the miR-489 nucleotide can be delivered by liposome delivery agents. Liposomes are generally derived from phospholipids or other lipid substances, and can be formed by mono- or multilamellar hydrated liquid crystals that are dispersed in an aqueous medium. Any non-toxic, physiologically acceptable and metabolisable lipid capable of forming liposomes can be used. In one embodiment lipids of useful liposomes can include phospholipids and/or phosphatidylcholines (lecithins), which can encompass both natural and synthetic materials.

Methods of treating breast cancer according to the present disclosure can include administering to a subject a therapeutically effective amount of an miR-489 nucleotide. It should be understood that both human and veterinary uses are contemplated. In one embodiment, an miR-489 nucleotide can be administered in conjunction with one or more other anti-cancer or chemotherapeutic agents as are generally known in the art.

The miR-489 may be delivered or administered acutely or chronically according to various delivery methods, including and without limitation sustained release methods, topical application (including dermal, transdermal, subcutaneous, etc), parenteral (including, for example, intraarterial, intravenous, intramuscular, subcutaneous), osmotic pumps, inhalation, oral, nasal, mucosal (including sublingual), or intracavitary routes, and so forth The most advantageous route for any given circumstance can be determined by those skilled in the art. For example, in circumstances where it is required that appropriate concentrations of the miR-489 are delivered directly to the site in the body to be treated, administration may be regional rather than systemic. Regional administration provides the capability of delivering very high local concentrations of the desired agent to the required site and thus is suitable for achieving the desired effect while avoiding exposure of other organs of the body to the compound and thereby potentially reducing side effects.

The miRNA-489 can be delivered in the form of a pharmaceutically acceptable composition that includes a suitable biologically acceptable carrier for the miRNA-489. A composition can be formulated in a variety of forms including solutions, suspensions, emulsions, and solid forms and are typically formulated so as to be suitable for the chosen route of administration, for example as capsules, tablets, caplets, elixirs for oral ingestion, in an aerosol form suitable for administration by inhalation (such as by intranasal inhalation or oral inhalation), ointment, cream, gel, jelly or lotion suitable for topical administration, or in an injectable formulation suitable for parenteral administration. The preferred route of administration will depend on a number of factors including the specific characteristics of the cancer to be treated and the desired outcome.

Compositions for parenteral delivery, e.g., via injection, can include pharmaceutically acceptable aqueous and non-aqueous carriers, diluents, solvents or vehicles such as, without limitation, water, ethanol, polyols (e.g., glycerol, propylene glycol, polyethylene glycol and the like), carboxymethylcellulose and suitable mixtures thereof, vegetable oils (e.g., olive oil) and injectable organic esters such as ethyl oleate. In addition, a composition can contain minor amounts of auxiliary substances such as wetting or emulsifying agents, pH buffering agents and the like that can enhance the effectiveness of the miR-489. Compositions may also contain adjuvants such as preservatives, wetting agents, emulsifying agents and dispersing agents.

Prevention of the action of microorganisms may be ensured by the inclusion of various antibacterial and antifungal agents such as paraben, chlorobutanol, phenol, sorbic acid and the like. It may also be desirable to include isotonic agents such as sugars, sodium chloride and the like.

A composition can include one or more oil-soluble antioxidants including, without limitation, butylated hydroxytoluene (BHT), ascorbyl palmitate, butylated hydroxyanisole (BHA), α-tocopherol, phenyl-a-naphthylamine, hydroquinone, propyl gallate, nordihydroguiaretic acid, and mixtures thereof as well as any other known oil-soluble antioxidant compatible with the other components of the compositions. Mineral oils, animal oils, vegetable oils and silicones can be incorporated in a topical creams or lotions as disclosed herein. In addition to such oils, other emollients and surface active agents can be incorporated in an emulsion.

Thickeners such as natural gums and synthetic polymers, as well as preservatives such as methylparaben, butyl paraben, propylparaben and phenyoxyethanol, coloring agents and fragrances can be included in a composition, for instance a composition for topical application such as a lotion.

A composition may also contain, as optional additions, one or more soluble or dispersible pharmaceutically acceptable ingredients generally used in pharmaceutical emulsion compositions. Typical such ingredients include, for example, a preservative or antioxidant such as methyl or propyl paraben, butylated hydroxyanisole, imidazolidinyl urea and the like; a water or oil soluble vitamin such as vitamin C, tocopheryl linoleate and the like; and/or a colorant, odorant, humectant, thickener and the like.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include com starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, α-tocopherol, ascorbic acid, methyl paraben, propylparaben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate. polyoxyethylene-sorbitan mono-or di-oleate, -stearate or -laurate and the like. Emulsions for oral administration may further comprise one or more emulsifying agents. Suitable emulsifying agents include dispersing agents as exemplified above or natural gums such as guar gum, gum acacia or gum tragacanth.

Each additive of a composition may generally constitute between about 0.05% to about 15% of the total weight of the formulation. In one embodiment, a composition can include an additive in an amount between about 0.05% and about 10% or between about 0.05% and about 8%, or between about 0.05% and about 7%, or between about 0.05% and about 6%, or between about 0.05% and about 5% of the total weight of the formulation.

According to one embodiment, methods can include a detection step to ascertain whether a subject has breast cancer. For example, a sample from a subject suspected of having cancer can be tested to determine the relative expression levels of miR-489, HER2 and/or SHP2. For example, a test sample from the animal demonstrating that the ratio of miR-489 to HER2 or SHP2 is about 0.5 or less, about 0.4 or less, or about 0.3 or less can be indicative of a breast cancer diagnosis.

Suitable biological samples include but are not limited to whole blood, non-heparinized plasma, serum, urine, sputum, phlegm, saliva, tears, and other bodily fluids. In important embodiments, the biological sample is a whole blood sample or a serum sample derived therefrom.

miRNA can be obtained from a biological sample using techniques used to harvest and/or isolate RNA generally. Harvest and isolation of total RNA from a sample is known in the art and reference can be made to standard RNA isolation protocols. The method does not require that miRNA be enriched from a standard RNA preparation. However, if desired, miRNA can be enriched using, for example, a YM-100 column. miRNA-489 levels may be detected using any number of assays known in the art. These assays include, without limitation, miRNA arrays (including those that are commercially available from sources such as Agilent and Illumina), reverse transcriptase polymerase chain reaction (RT-PCR), quantitative real-time reverse transcriptase PCR (qPCR) using TaqMan microRNA assays (including those commercially available from sources such as Applied Biosystems, Foster City, Calif., USA), in situ hybridization, Northern hybridization, hybridization protection assay (HPA) (GenProbe), branched DNA (bDNA) assay (Chiron), rolling circle amplification (RCA), Invader assay (ThirdWave Technologies), and/or Oligo Ligation Assay (OLA), hybridization, and the like. Some methods measure miRNA levels by amplifying all or part of miRNA nucleic acid sequences such as mature miRNAs, precursor miRNAs, and primary miRNAs. Suitable nucleic acid polymerization and amplification techniques include reverse transcription (RT), polymerase chain reaction (PCR), real-time PCR (quantitative PCR (q-PCR)), nucleic acid sequence-base amplification (NASBA), ligase chain reaction, multiplex ligatable probe amplification, invader technology (Third Wave), rolling circle amplification, in vitro transcription (IVT), strand displacement amplification, transcription-mediated amplification (TMA), RNA (Eberwine) amplification, and other methods that are known to persons skilled in the art. One or more amplification methods may be used, such as reverse transcription followed by real time PCR.

The present disclosure may be better understood with reference to the Example set forth below.

EXAMPLE

Cell Lines and Reagents

MCF7 vect and MCF7 HER2 cell lines were grown in DMEM supplemented with 10% FBS and 5 µg/ml insulin. Other breast cancer cell lines AU-565, BT-474, HCC1954, T47D, ZR-75-1, HCC1569 and ZR-75-3 were purchased from ATCC and cultured in RPMI-1640 containing 10% FBS. All cells were cultured at 37° C. in a humidified incubator containing 5% $CO_2$. MDA-MB-468, MDA-MB-231, MDA-MB-435, SK-BR-3 and MDA-MB-453 were purchased from ATCC and cultured in DMEM containing 10% FBS. All cells were cultured at 37° C. in a humidified incubator containing 5% $CO_2$. DOTAP (N-[1-(2,3-Dioleoyloxy) propyl]-N, N,N- trimethylammonium methyl-sulfate) and cholesterol were purchased from Avanti Polar Lipids. Protamine sulfate was from Sigma-Aldrich and Sodium hyaluronate was purchased from Lifecore biomedical.

Plasmid Constructs

A 650 bp long 3' UTR of human HER2 was amplified from genomic DNA and cloned into the pGL3-promoter vector at the same Xba I and BamH I sites. For the mutation analysis putative miR-489 target site within 3'UTR of HER2 was mutated by Phusion site directed mutagenesis kit (Thermofisher Cat# F-541). All sequences were verified by direct sequencing of the plasmids.

Stable Cell Line Generation 293T cells were transfected with 3 µg of SHP2 (Addgene #8329)/HER2 plasmid, 3 µg of VSVG plasmid and 2.5 µg of ECO plasmid using 17 µl of Lipofectamine2000 for 48 hour. After 48 hour, supernatants were collected and spun down at 10,000 RPM at 4° C. to discard any cell debris. MDA-MB-231 cells were infected with SHP2 and HER2 lentivirus for 48 hour. Infected cells needed to be puromycin resistant and therefore cells were treated with puromycin for one week.

Preparation of miR-489-Delivering Nanoparticle

Liposomes were prepared as described elsewhere with some modifications. Briefly small unilamellar liposomes consisting of DOTAP and cholesterol were prepared by thin film hydration method. The film was hydrated with nuclease free water and sonicated in a bath type sonicator for 5 min followed by extrusion through 200 and 50 nm membrane filters. The total lipid concentration of the liposomes was fixed at 28.6 mM (20 mg/ml).

Clinical Tissues and Fluorescent In Situ Hybridization (FISH)

Tissue samples were randomly collected from patients who were diagnosed with invasive breast ductal carcinoma between 2003 and 2007. Tissue samples from breast cancer patients who underwent surgery in 2008 were obtained.

Tissue sections were dewaxed and rehydrated with phosphate buffered saline (PBS) and fixed using 4% paraformaldehyde (PFA). Next, tissue sections were treated with proteinase K (50 µg/µl, life technology) for 15 min at 37° C. Acetylation of tissue sections was performed with 0.1M triethanolamine/0.25% acetic anhydride for 5 min. Sections were washed once with PBS. Before proceeding with hybridization step, hybridization buffer was prepared by mixing 250 µl of formamide, 250 µl of 20×SSC, 50× Denhard't solution (life technology), 12.5 µl of t-RNA (Roche), 2.5 µl of Herring Sperm DNA (Promega D1815), 0.02 gm of blocking reagent (Roche) and 30 µl of RVC (Fisher) in 1 ml. Sections were pre- hybridized with hybridization buffer for 2 h at room temperature. LNA-substituted DNA oligonucleotide probe for miR-489 was obtained from Exiqon (Cat#38599-01) labeled with digoxigenin at the 5' terminus. Probes were denatured at 95° C. for 5 min, and then chilled on ice for 5 min. Total of 100 µl diluted probe was added to cover tissue area. Slides were kept in the hybridization chamber and incubated in oven at 55° C. overnight. The following day, sections were washed once with 5×SSC for 7 min and twice each with 1×SSC (7 min) and 0.2×SSC (7 min) at 57° C., followed by two 7 min washes with 0.2×SSC at room temperature and final wash with 1×PBS. Sections were blocked with blocking reagent (life technology: E-6604) for 1 hour at room temperature, followed by incubation with anti-DIG AP labeled primary antibodies for 1 h at room temperature (Roche: 11093274910). Sections were washed with 1×PBS for 5 min and developed for microscopic visualization using ELF-97 kit from Life technology.

Statistical Analyses

Statistical analyses were conducted with R and GraphPad software packages (GraphPad). A Student t test or ANOVA test was used for comparison of quantitative data. The linear correlations between CALCR and miR-489 ligand expression in primary breast cancer tissues were evaluated with Pearson correlation coefficient analysis. The clinical effect of the gene expression profiles of miR-489 was further evaluated using two published datasets: Dvinge et al. (Nature. 2013; 497(7449):378-382) 1302 breast cancer patients, and Rinaldis et al. (BMC genomics. 2013; 14:643) 181 breast cancer patients. The patient samples were stratified into three equal groups based on the expression levels of miR-489. The two compared groups are the third of patients with the highest expression levels (high) versus the third of patients with the lowest expression (low). Overall survival was estimated using the Kaplan-Meier method and compared with log-rank tests. Univariate regression analysis and multivariate Cox PH regression analysis were performed to demonstrate the correlation between the patient survival and miR-489 while accounting for other potential predictors (covariates). The stepwise Akaike Information Criteria (AIC) method with "both" direction search was used with R step AIC function in the predictor variable selection during the multivariate regression. The selected model was assessed with the overall Goodness-of-fit test. Chi-square tests were made with the Schoenfeld residuals to check the proportional hazard assumption of the selected model. Values of $P<0.05$ were considered significant (**, $p<0.01$; *, $p<0.05$)

Other Methods

Quantitative real-time RT-PCR analysis, Immunohistochemistry staining (IHC), Western Blot analysis, Fluorescence-Activated Cell Sorting (FACS) assay, Luciferase assay and Xenograft experiments were performed using standard protocol.

Results

Screening and Identification of HER2-Regulated miRNAs in Breast Cancer Cells

Figure 3:
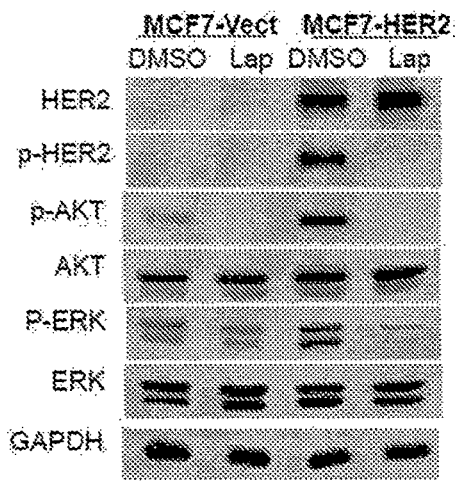
FIG. 3 presents Western blot analysis of HER2, p-HER2, p-AKT, Total AKT, p-ERK, Total ERK and GAPDH from total protein lysates isolated from MCF7 Vect and HER2 cells treated with 2 µM lapatinib (HER2 activation inhibitor).
Figure 4:
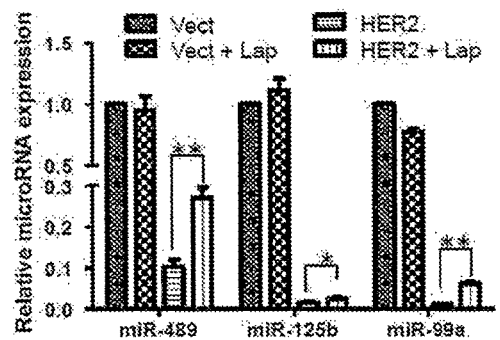
FIG. 4 presents qRT-PCR analysis of selective downregulated miRNAs whose expression was rescued by lapatinib treatment of MCF- HER2 cells. All data are representative of three independent experiments.

To identify specific miRNAs that may be involved in promotion of breast cancer progression, expression profiles of several (~200) miRNA were screened and compared for HER2 over-expressing and control MCF7 cells using quantitative RT-PCR (qRT-PCR) analysis. It was found that 21 of dysregulated miRNAs were significantly upregulated, whereas 19 were down regulated in MCF7 HER2 cells compared to the MCF7 Vect cells. Many of the upregulated miRNAs were known oncomiRs in breast cancer, such as miR-200, miR-141 and miR-223. Also, many of the down-regulated miRNAs in MCF7 HER2 cells were known tumor suppressors, such as miR-125b, miR-31 and miR-99a. To determine specific miRNAs truly driven by HER2 signaling, the HER2 kinase activity was blocked by treating MCF7 vect and MCF7 HER2 cells with EGFR/HER2 dual inhibitor lapatinib for 48 h. Lapatinib treatment resulted in the almost complete blockade of HER2, AKT and Mitogen activated protein kinase (MAPK) phosphorylation (FIG. 3). qRT-PCR was then performed using the RNA from lapatinib treated vect and HER2 cells to identify miRNAs that restore their expression by inhibition of HER2 signaling (data not shown). The qRT-PCR data demonstrated that miR-489, miR-125b and miR-99a at least partially restored the expression profile after inhibition of HER2 phosphorylation (FIG. 4).

HER2 Negatively Regulates miR-489 Mainly Via the MAPK Pathway

Figure 5:
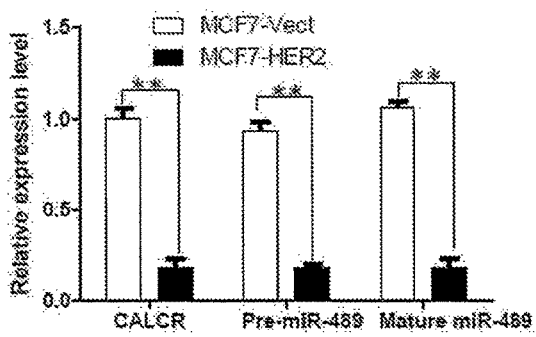
FIG. 5 presents real-time PCR analysis of calcitonin receptor (CALOR) mRNA, pre-miR-489 and mature miR-489 RNA levels in MCF7-HER2 and MCF7-vect cells.
Figure 6:
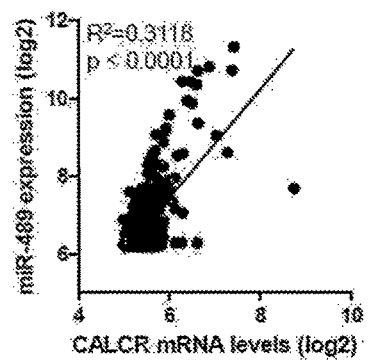
FIG. 6 illustrates the correlation between CALOR mRNA and mature miR-489 in clinical breast cancer tissue. The linear correlations between CALOR and miR-489 ligand expression in primary breast cancer tissues were evaluated with Pearson correlation coefficient analysis using a public dataset.

The miR-489 gene sequence is located in the intronic region of calcitonin receptor (CALOR) gene. To find whether HER2 affects the expression of miR-489 at transcriptional level, the expression levels of mature miR-489, pre-miR-489 and CALOR mRNA were quantified in MCF7 vect and HER2 cells using gRT-PCR (FIG. 5). Data demonstrated that expression of CALCR mRNA, pre-miR-489 and mature miR-489 are down regulated to a similar extent (FIG. 4), suggesting that expression of miR-489 may be controlled at the transcription level. The strong positive correlation between the expression levels of CALOR and miR-489 in clinical samples further confirmed this conclusion (FIG. 6).

To determine the role of a particular signaling pathway in miR-489 transcriptional regulation, MCF7 HER2 cells were treated with the HER2-downstream signaling pathways inhibitors targeting NF-κB (Bay-11-7082), PI3K (LY294002), AKT1 (SC-66), MEK (U0126), MAPK (PD0325901), SRC (PP2), p38 (SB-203580), and STAT3 (Stattic) signaling. The qRT-PCR indicated that miR-489 levels were most significantly rescued by two inhibitors, both targeting the MEK-ERK signaling (FIG. 7). These results led us to believe that MEK-ERK signaling might be crucial in controlling the miR-489 transcription, although STAT3 and SRC pathways may also be involved in its regulation.

To further validate that miR-489 might be regulated by MEK-ERK signaling possibly through HER2 down-regulation, cells were treated with si-AKT1 and si-SHC to block two downstream effectors of HER2 signaling. As shown in FIG. 8, treatment of si-AKT1 or si-SHC resulted in decreased AKT1 expression and decreased activation of p-ERK respectively. However, expression of miR-489 was rescued only by si-SHC knockdown and not by AKT1 knockdown. Furthermore, to understand triggering of which pathway results in miR-489 down regulation, proteins were isolated from 13 breast cancer cell lines and performed western blotting for p-ERK and pAKT. Protein expression data was quantified and correlated with the expression of miR-489 in each cell line. The statistical data clearly demonstrated that p-ERK, not p-AKT, was negatively correlated with the levels of miR-489 in all 13 breast cancer cell lines (FIG. 9, FIG. 10). Overall, these results clearly demonstrated that miR-489 expression is transcriptionally regulated mainly by the HER2-driven MAPK downstream signaling.

Overexpression of miR-489 Inhibits Cell Growth In Vitro

Figure 11:
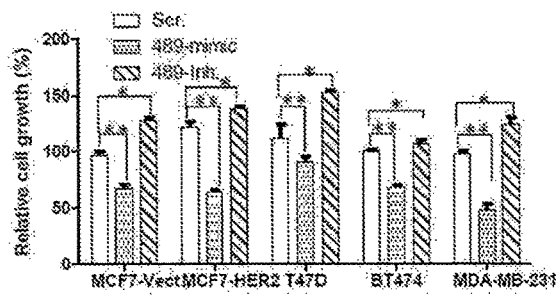
FIG. 11 presents the results of an MTT cell viability assay showing the rate of cell proliferation of MCF7-Vect and HER2, BT-474, T47D and MDA-MB-231 cells transfected with miR-489 mimic or inhibitor for 72 h.
Figure 12:
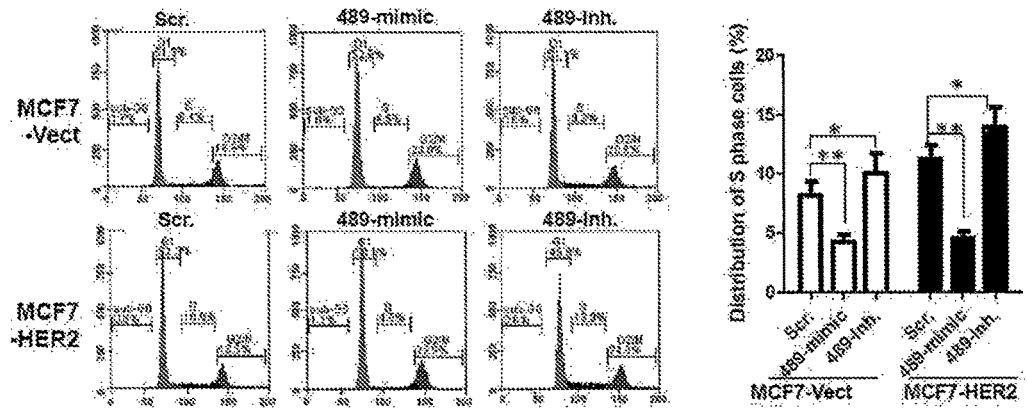
FIG. 12 presents the cell cycle analysis of cells transfected with miR-489 scramble, miR-489 mimic or miR-489 inhibitor using FACS. Representative FACS profiles (left graphs) and average percentages of S phase cells (right graphs) are shown.

To explore the biological function of miR-489 in breast cancer, breast cancer cells were transiently transfected with miR-489 mimic, scramble or inhibitor (obtained from Darmacom; mimic Cat#, c-300749-07-0010; inhibitor cat#, IH-300749-08-0010) and cell growth was measured by MTT assay. Results clearly indicated that miR-489 expression inhibited cell proliferation in all of the four tested breast cancer cell lines and conversely, knockdown of miR-489 increased cell proliferation (FIG. 11). However, significant changes were not observed in cellular morphology and the number of floating cells. To test the possibility that miR-489 may regulate cell cycle progression, the cell cycle profiles were examined by FACS analysis. A dramatic decrease or increase in the S phase population of miR-489 mimic and miR-489 inhibitor transfected cells respectively were observed (FIG. 12). Consistently, overexpression of miR-489 appeared not to induce apoptosis, which is evident by slight changes in the Sub-G0 cell populations. A similar trend was observed in both MCF7-vect and MCF7-HER2 cells although changes were more dramatic in MCF7-HER2 cells.

Next, to examine whether miR-489 inhibits colony formation ability of cancer cells, both MCF7 and MDA-MB-231 cells transfected with either the scramble, mimic or miR-489 inhibitor were used to perform colony formation assay. Results clearly demonstrated that cells transfected with miR-489-mimic yielded significantly less colonies compared to the cells transfected with scramble miRNA (FIG. 13). Conversely, cells transfected with inhibitor of miR-489, had the opposite effect and resulted in forming more colonies than the cells transfected with scramble miRNA. Taken together, increased expression of miR-489 in breast cancer cells resulted in inhibited cell proliferation and transformation.

miR-489 Regulates HER2 Signaling Pathway by Directly Targeting HER2 and its Downstream Gene Shp2

According to the miR walk pathway target prediction, HER2 pathway can be potentially targeted by miR-489. To verify whether miR-489 has any effect on HER2 signaling, MCF7 Vect and HER2 cells were transfected with mimic or inhibitor of miR-489 and total protein was isolated after 72 h. Western blotting analysis was performed to examine the HER2 signaling in the transfected cells (FIG. 14). Results indicated that miR-489 mimic dramatically impaired HER2 signaling as evident by reduced HER2, phospho-HER2, SHP2, phosphor-AKT and phosphor-ERK (FIG. 14). Conversely, miR-489 inhibitor transfected cells exhibited reversed effect on HER2 signaling compared to miR-489 mimic. Moreover, it was also observed that expression of total HER2 and SHP2 were reduced in miR-489 mimic transfected cells and elevated in the miR-489 inhibitor transfected cells (FIG. 14).

Previous studies showed that miR-489 can downregulate SHP2 expression in hypopharyngeal squamous cell carcinomas by directly binding to its 3'UTR. We confirmed that overexpression of miR-489 reduced SHP2 expression in breast cancer cell lines at both mRNA and protein levels. To examine the similar effect of mimic-489 treatment on the expression of HER2, other breast cancer cell lines, AU-565, BT-474, HCC-1954 and ZR-75-1 cells were treated with mimic-489 for 72 hours to isolate total protein and RNA. Western blotting data demonstrated that the expression of HER2 was decreased in all tested cell types treated with mimic-489 (FIG. 15). Together, the results strongly suggested that miR-489 may directly target HER2 and SHP2 in breast cancer cells and regulates its expression. By searching through 3'UTR sequence of HER2, a potential partially complementary miR-489 binding site was identified. To demonstrate that this site is functional, the dual luciferase assay was performed using reporter constructs containing ~400 bp long wt 3'UTR or mutant 3' UTR of HER2. The data showed that in the presence of miR-489, luciferase activity of wt HER2 3'UTR and not the mutant HER2 3'UTR is significantly reduced (FIG. 16). These results clearly demonstrated that miR-489 inhibits HER2 expression by directly binding to its 3'UTR region.

Previous, studies have validated one of the downstream effector of HER2 signaling SHP-2 as the direct target of miR-489. SHP-2 is known to affect ERK signaling. Since p-ERK levels were also inversely correlated with the expression of miR-489, it was hypothesized that miR-489 affects ERK signaling by downregulating the expression of HER2 and SHP2. Using lentiviral system, MDA-MB-231 cells over-expressing (OE) either HER2 or SHP2 were constructured (FIG. 17). Also, level of p-ERK was increased in both SHP2 OE cells and HER2 OE cells as shown in western blot (FIG. 17). To demonstrate the effect of SHP2 OE or HER2 OE on cell survival against miR-489, SHP2 and HER2-overexpressing MDA-MB-231 cells were transfected with either mimic or inhibitor of miR-489. MTT data indicated that both SHP2 and HER2 overexpression led to the increased cell survival significantly when compared to the vector control cells in the presence of miR-489 mimic (FIG. 18). These results overall indicated a double feedback loop model in which HER2 and SHP2 activates ERK signaling which results in the inhibition of miR-489 expression, while miR-489 targets both SHP2 and HER2 simultaneously to affect the ERK signaling and therefore decrease the cell proliferation (FIG. 1).

Over Expression of miR-489 Inhibits Tumor Growth In Vivo

Figure 19:
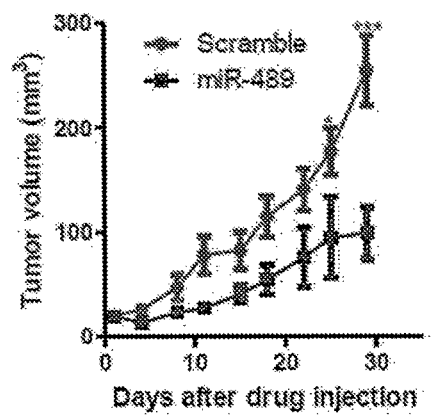
FIG. 19 illustrates the rate of tumor volume change following delivery of either miR-489 or scramble miR-489. After the tumors were palpable, all 7 tumor sites were injected with miR-489 or scramble miRNA encapsulated in a nanoparticle delivery system. The treatment starting day was referred to as 'Day zero' in the figure.
Figure 21:
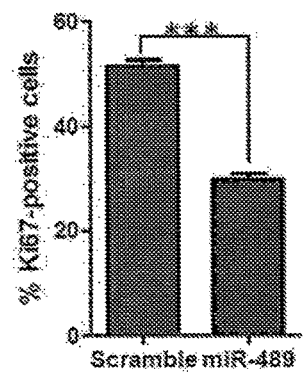
FIG. 21 presents a graph showing number of Ki-67 positive cells in tumors treated with nanoparticle-delivered miR-489 or scrambled miRNA.
Figure 20:
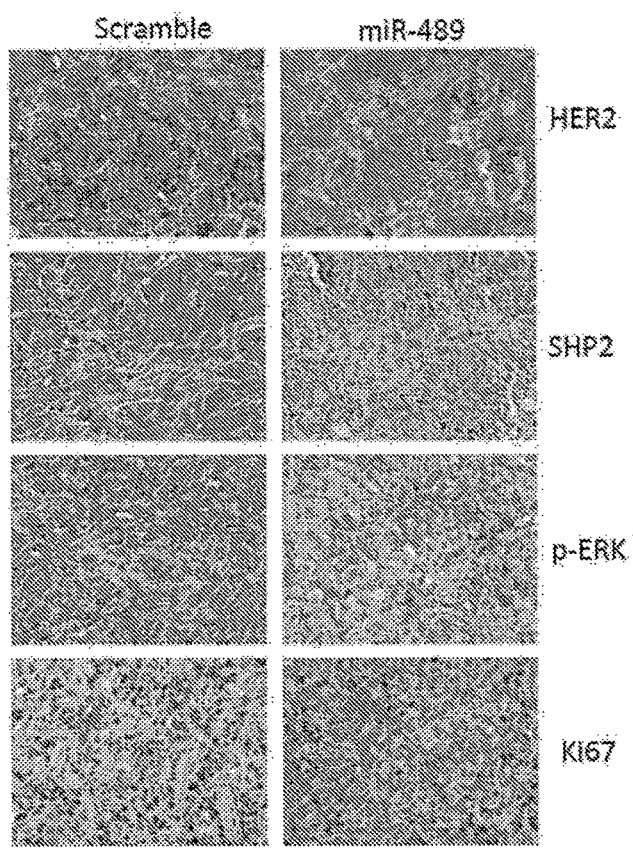
FIG. 20 presents IHC analysis of HER2, SHP2, p- ERK and Ki-67 cells in tumors treated with nanoparticle-delivered miR-489 or scrambled miRNA.

Since miR-489 inhibited cell proliferation and decreased transforming capacity of cells to form colony in vitro (FIG. 13), the ability to inhibit tumor growth in vivo was assessed. To explore the possibility to use miR-489 for therapy, a nanoparticle delivery system was developed to deliver miR-489 into tumor cells. The nanoparticle packaged with miR-489 showed similar size distribution as control nanoparticles. Treatment of cells with increased concentration of nanoparticle resulted in a decrease in HER2 expression levels in a dose-dependent manner, indicating that nanoparticles can effectively deliver miR-489 into tumor cells. In this xenograft experiment, athymic nude mice were injected with ~2 million HCC1954 cells and monitored for tumor growth randomly assigned in 2 groups. After tumors were palpable, both group one and two were given the intratumoral injection of nanoparticles packaged with scramble miRNA or mimic-489 respectively every 3 days. The tumor volume data indicated that in the last two time points tumor sizes of the mimic-489 injected group of mice were significantly (p<0.001) smaller than the scramble injected group of mice (FIG. 19). Moreover, the IHC data also revealed that HER2 and SHP2 expression was lower in miR-489 injected tumors compared to the tumors injected with scramble (FIG. 20). The IHC data indicated that p-ERK level was reduced in miR-489 injected tumors compared to the tumors injected with scramble. Also, number of ki-67-positive cells was significantly lower in miR-489 injected tumors when compared to the scramble injected tumors (FIG. 21). Together, these data demonstrated that miR-489 delivered through nanoparticles inhibited tumor growth in xenografts by decreasing cell proliferation at least partially by blocking the HER2-, SHP2-MAPK signaling axis.

Low Expression of miR-489 in Primary Breast Cancer is Associated with Aggressive Phenotypes and Poor Clinical Outcomes To explore the clinical relevance of miR-489 expression in breast cancer, quantitative RT-PCR analysis was performed of cDNAs generated from 11 pairs of samples each including breast cancer tissue and corresponding adjacent normal tissue. Compared to the adjacent normal tissues, primary breast cancers expressed lower levels in 9 out of 11 pairs of samples (FIG. 22). To further validate that loss of miR-489 expression in breast cancer epithelial cells, in situ fluorescent hybridization was carried out on breast cancer tissue and adjacent normal tissues. High levels of miR-489 expression were detected in normal epithelia cells and occasionally myoepithelial cells, however, the staining signal intensities were weak in the stromal and tumor areas (FIG. 23). Furthermore, correlation were examined between miR-489 expression level and other clinical parameters including overall survival, HER2 status, metastasis, grade and stages. It was found that there was an inverse correlation between the expression of miR-489 and HER2 in clinical samples as indicated by the in vitro data. Loss of miR-489 expression was especially associated with tumor in higher grades and higher stages. It was also found that the expression levels of miR-89 tended to be lower in HER2-positive and basal subtypes compared to both luminal and normal-like subtypes of breast cancer (FIG. 24). Given that the expression status of miR-489 tends to be associated with the aggressive subtypes of breast cancers, the Kaplan-Meier survival analysis was performed to further evaluate the prognostic value. As expected, patients with low miR-489 expression had a relatively poor overall survival than those with high miR-489 expression (FIG. 25). In addition, multivariate analysis revealed that miR-489 expression was an independent prognostic factor to predict overall patient survival (Table 1, below).

TABLE 1

| Variables | HR | CI (95%) | P value |
| --- | --- | --- | --- |
| Tumor size (≤2 cm/≥2 cm) | 1.016 | 1.006-1.026 | <0.001 |
| Tumor Grade | | | |
| Grade (I/II) | 1.802 | 0.902-3.601 | 0.095 |
| Grade (I/III) | 2.422 | 1.221-4.804 | 0.011 |

TABLE 1-continued

| Variables | HR | CI (95%) | P value |
|---|---|---|---|
| Tumor Stage | | | |
| Stage (I/II) | 1.205 | 0.804-1.807 | 0.367 |
| Stage (I/III, IV) | 1.860 | 1.040-3.326 | 0.036 |
| HER2 status (negative/positive) | 1.691 | 1.232-2.323 | 0.001 |
| Lymph node (negative/positive) | 1.769 | 1.265-2.476 | <0.001 |
| miR-489 (low/high) | 0.606 | 0.433-0.850 | 0.004 |

Together, the results support the thesis that miR-489 can act as a tumor suppressor and loss of miR-489 in breast cancer may contribute to breast cancer progression and metastasis.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for decreasing breast cancer cell proliferation, the method comprising:
   determining in a breast cancer cell population the over-expression of one or more of SHP2, ERK, and p-ERK; and
   thereafter, delivering a polynucleotide to the population of breast cancer cells, the polynucleotide comprising a microRNA-489 or a microRNA-489 mimic, or encoding the microRNA-489 or the microRNA-489 mimic, wherein following the delivery of the polynucleotide, the breast cancer cells exhibit a decrease in proliferation rate.

2. The method of claim 1, wherein the polynucleotide is a DNA sequence.

3. The method of claim 2, wherein the polynucleotide is delivered in conjunction with an expression system.

4. The method of claim 2, the polynucleotide comprising SEQ ID NO: 1.

5. The method of claim 1, wherein the polynucleotide is an RNA sequence.

6. The method of claim 5, wherein the RNA sequence comprises a pri-miRNA-489, a pre-miRNA-489, or a mature single strand miRNA-489.

7. The method of claim 5, the polynucleotide comprising SEQ ID NO: 2.

8. The method of claim 1, wherein the breast cancer cells are also determined to over-express HER2.

9. The method of claim 1, wherein the polynucleotide is the microRNA-489 mimic.

10. The method of claim 1, wherein the method comprises an in vivo delivery of the polynucleotide to the population of breast cancer cells.

11. The method of claim 1, wherein the method comprises an ex vivo delivery of the polynucleotide to the population of breast cancer cells.

12. The method of claim 1, wherein the method comprises an in vitro delivery of the polynucleotide to the population of breast cancer cells.

13. The method of claim 1, wherein the polynucleotide is delivered as a component of a transgenic cell.

14. The method of claim 1, wherein the polynucleotide is delivered within a delivery vehicle.

15. The method of claim 14, wherein the delivery vehicle comprises a micro- or nano-sized vesicle.

16. The method of claim 1, further comprising prior to the delivery of the polynucleotide to the population of breast cancer cells, obtaining a sample from a subject and determining the ratio of microRNA-489 concentration to HER2 concentration in the sample.

* * * * *